United States Patent
Malone et al.

(10) Patent No.: US 10,201,699 B2
(45) Date of Patent: Feb. 12, 2019

(54) IMPLANTABLE THERAPY LEAD INCLUDING BI-DIRECTIONAL ROTARY BLOOD RING SEAL

(71) Applicant: PACESETTER, INC., Sylmar, CA (US)

(72) Inventors: Matthew Malone, Valencia, CA (US); Tyler Smith, Mission Hills, CA (US); Tyler Strang, Valencia, CA (US); Xiangqun Chen, Santa Clarita, CA (US); Steven R. Conger, Agua Dulce, CA (US); Jeremy Hurwitz, Pasadena, CA (US)

(73) Assignee: PACESETTER, INC., Sylmar, CA (US)

( * ) Notice: Subject to any disclaimer, the term of this patent is extended or adjusted under 35 U.S.C. 154(b) by 216 days.

(21) Appl. No.: 15/051,522

(22) Filed: Feb. 23, 2016

(65) Prior Publication Data
US 2017/0239465 A1    Aug. 24, 2017

(51) Int. Cl.
*A61N 1/05* (2006.01)

(52) U.S. Cl.
CPC ............. *A61N 1/0573* (2013.01); *A61N 1/05* (2013.01); *A61N 1/056* (2013.01)

(58) Field of Classification Search
CPC ........ A61N 1/05; A61N 1/3752; A61N 1/056; A61N 1/0573; A61N 1/3727; A61N 1/0517
See application file for complete search history.

(56) References Cited

U.S. PATENT DOCUMENTS

2002/0188338 A1\* 12/2002 Bischoff ................ A61N 1/056
                                                            607/122
2007/0100386 A1\* 5/2007 Tronnes ............... A61N 1/3752
                                                            607/37

\* cited by examiner

*Primary Examiner* — Michael D Abreu

(57) ABSTRACT

A therapy lead has a distal header, a helix-shaft assembly, and a ring seal. The distal header has a cylindrical passage, and the helix-shaft assembly has a shaft and a helical anchor distally extending from the shaft. The shaft extends through the cylindrical passage. The ring seal circumferentially extends about the shaft and inside the cylindrical passage. The ring seal has a proximal face, a distal face, an outer circumferential surface, an inner circumferential surface, and a side wall. The distal face is opposite the proximal face. The outer circumferential surface extends between the proximal face and distal face. The inner circumferential surface is opposite the outer circumferential surface and extends between the proximal face and distal face. The inner circumferential surface defines a center hole of the ring seal that extends between the proximal face and distal face. A side wall extends in a continuous ring about the center hole and is defined by the proximal face, the distal face, the outer circumferential surface, and the inner circumferential surface. The side wall includes a radial cross section that is at least generally chevron-shaped.

20 Claims, 9 Drawing Sheets

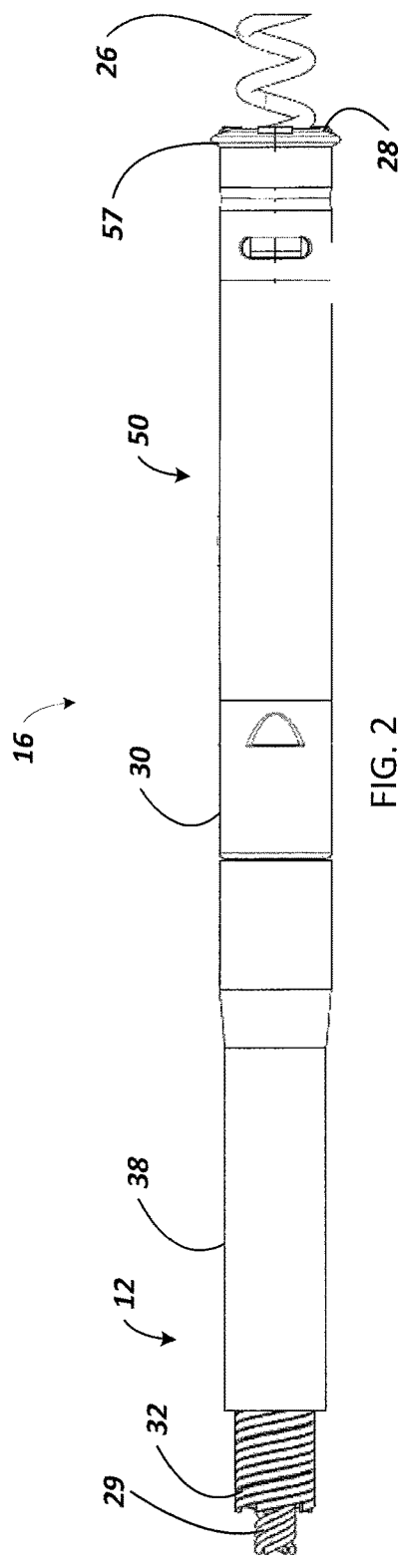
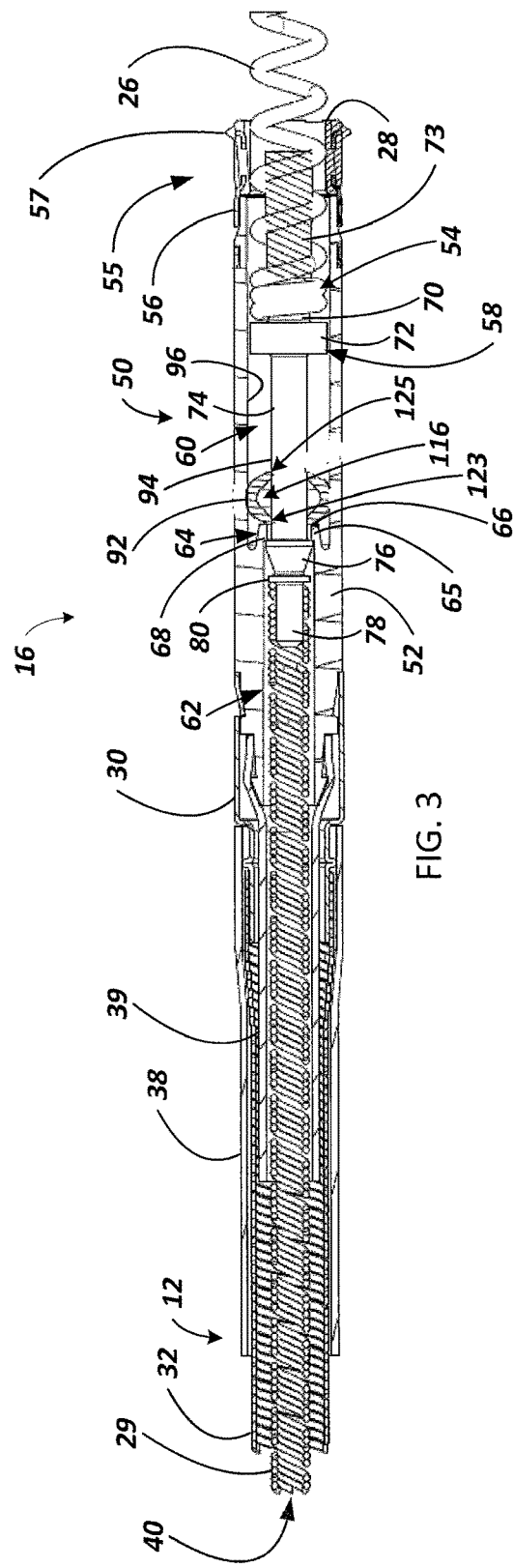
FIG. 2
FIG. 3

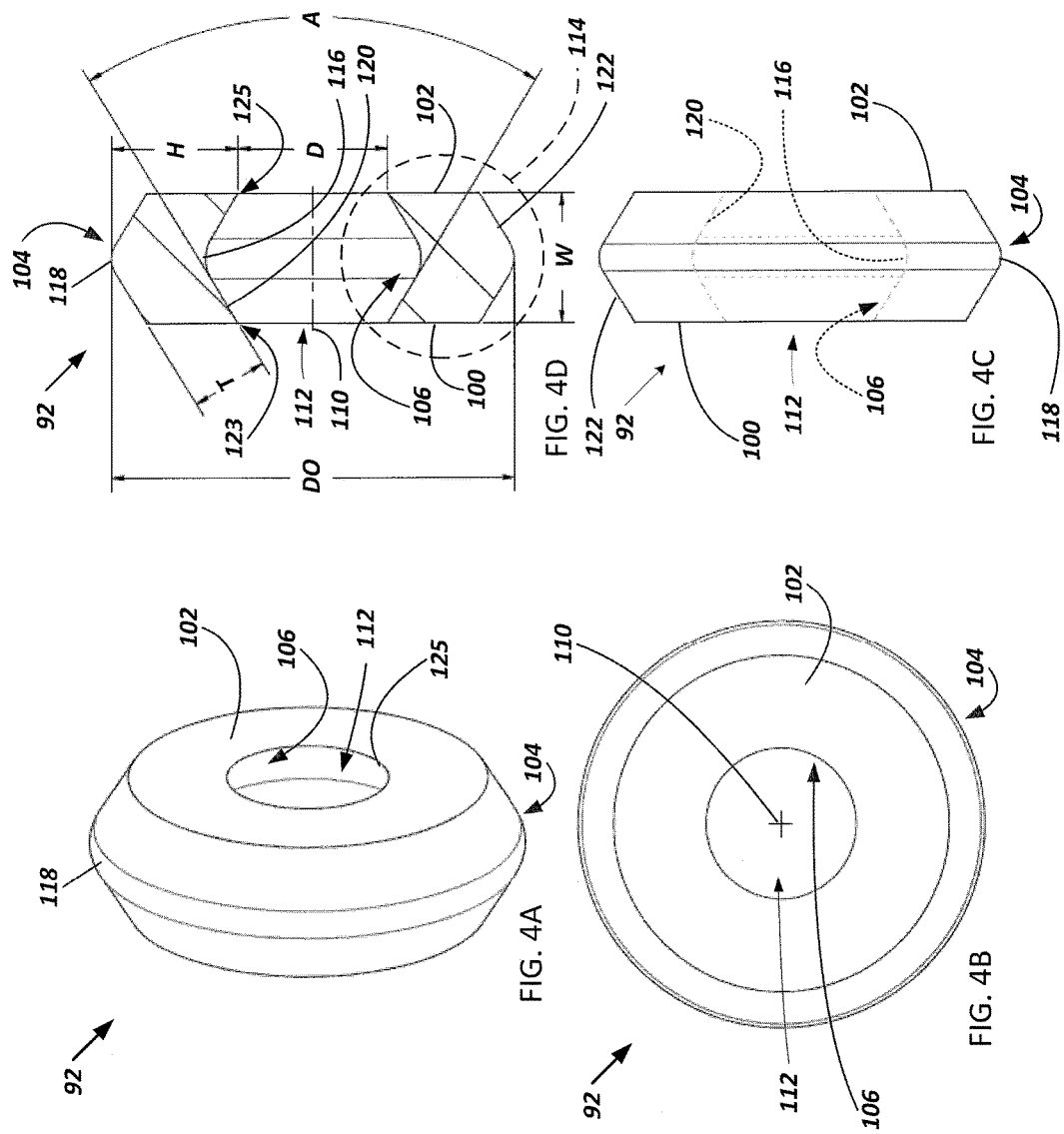

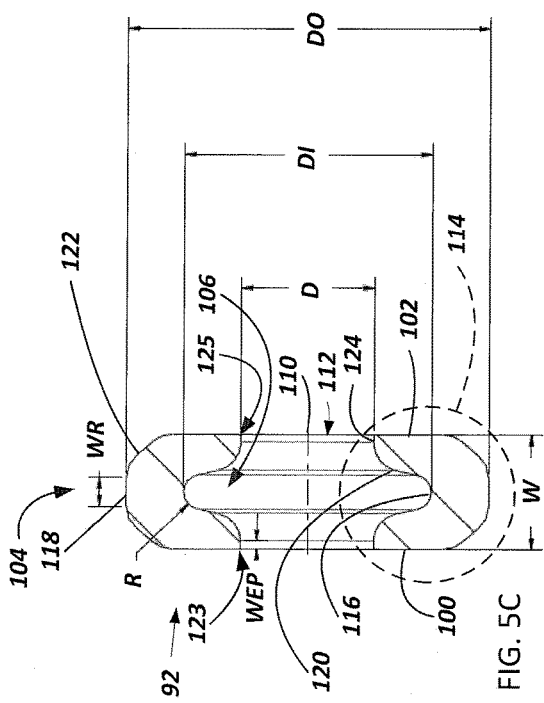
FIG. 5C
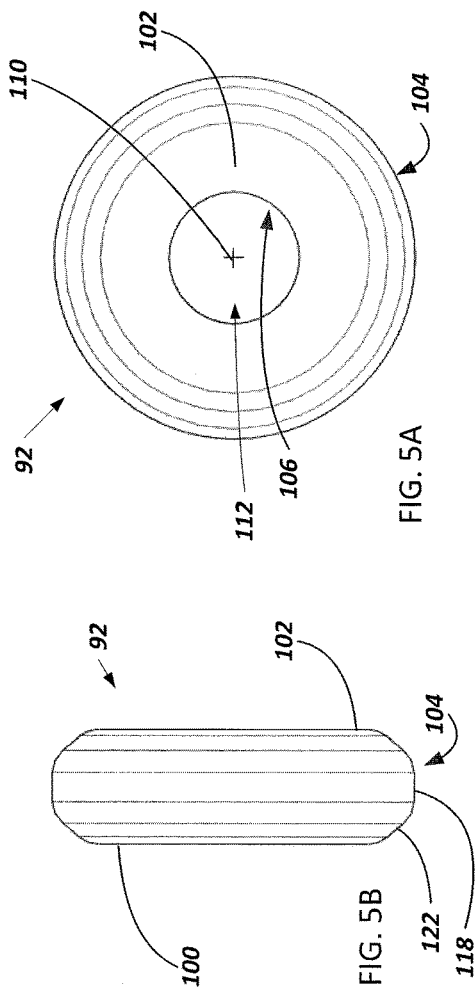
FIG. 5A
FIG. 5B

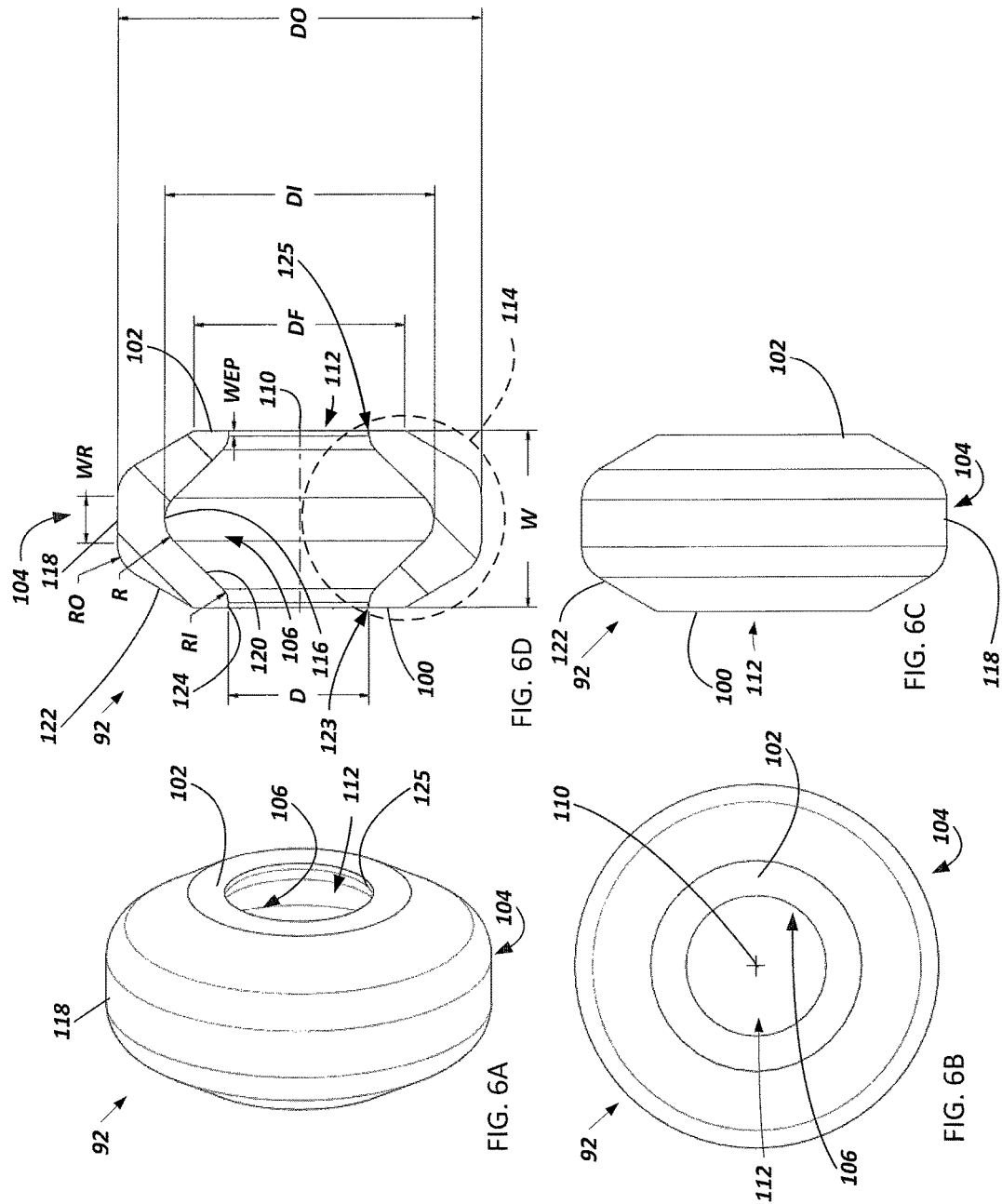

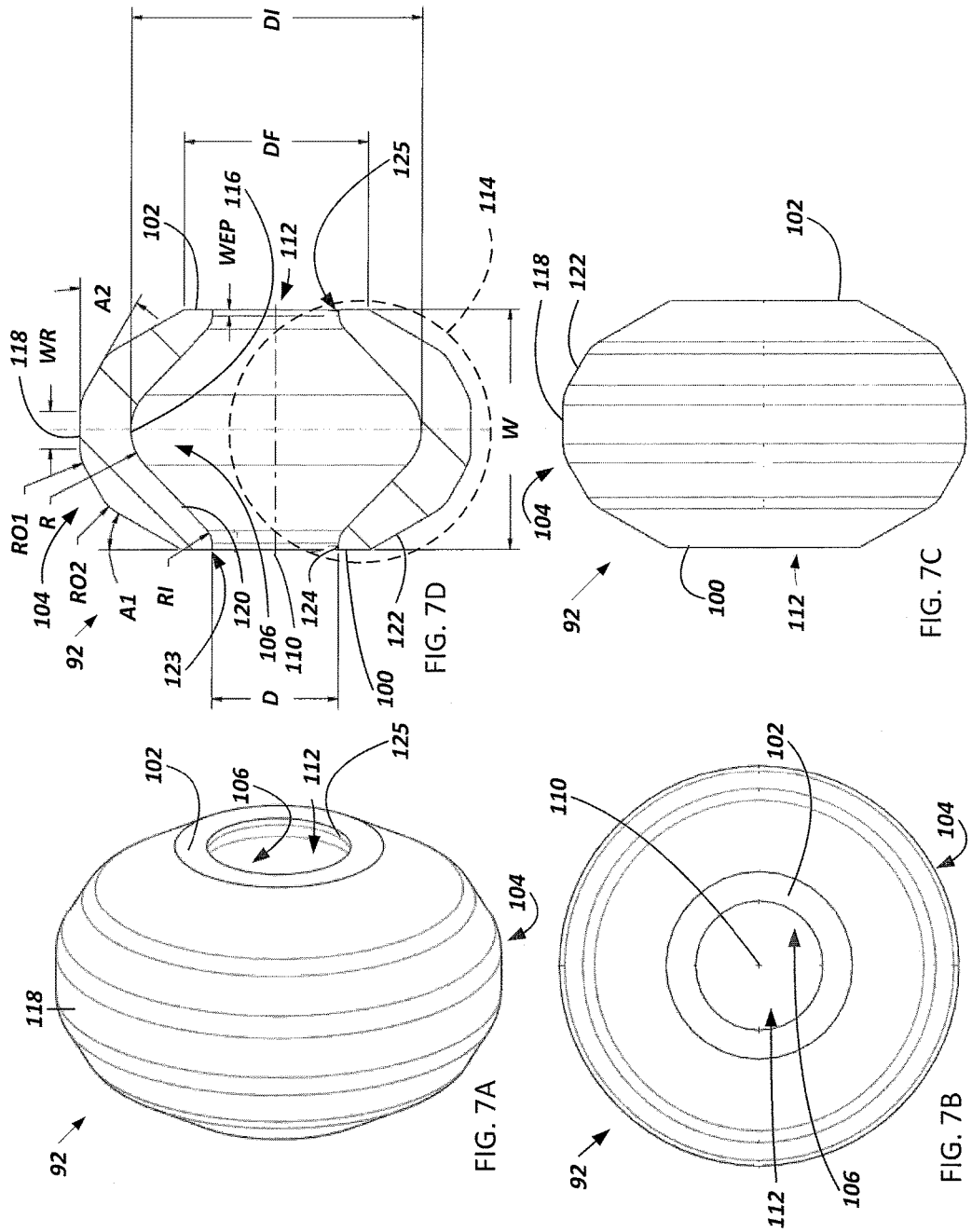

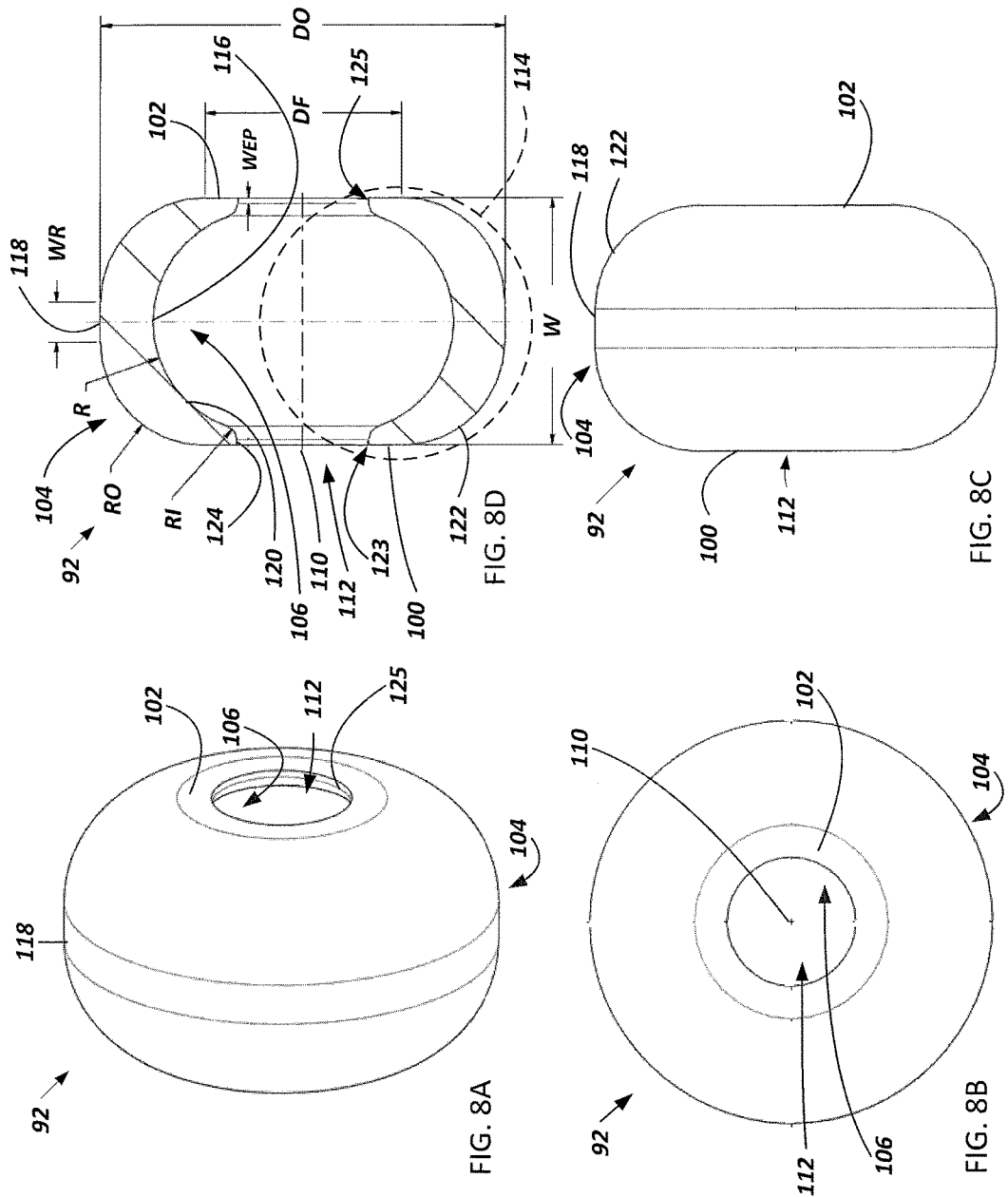

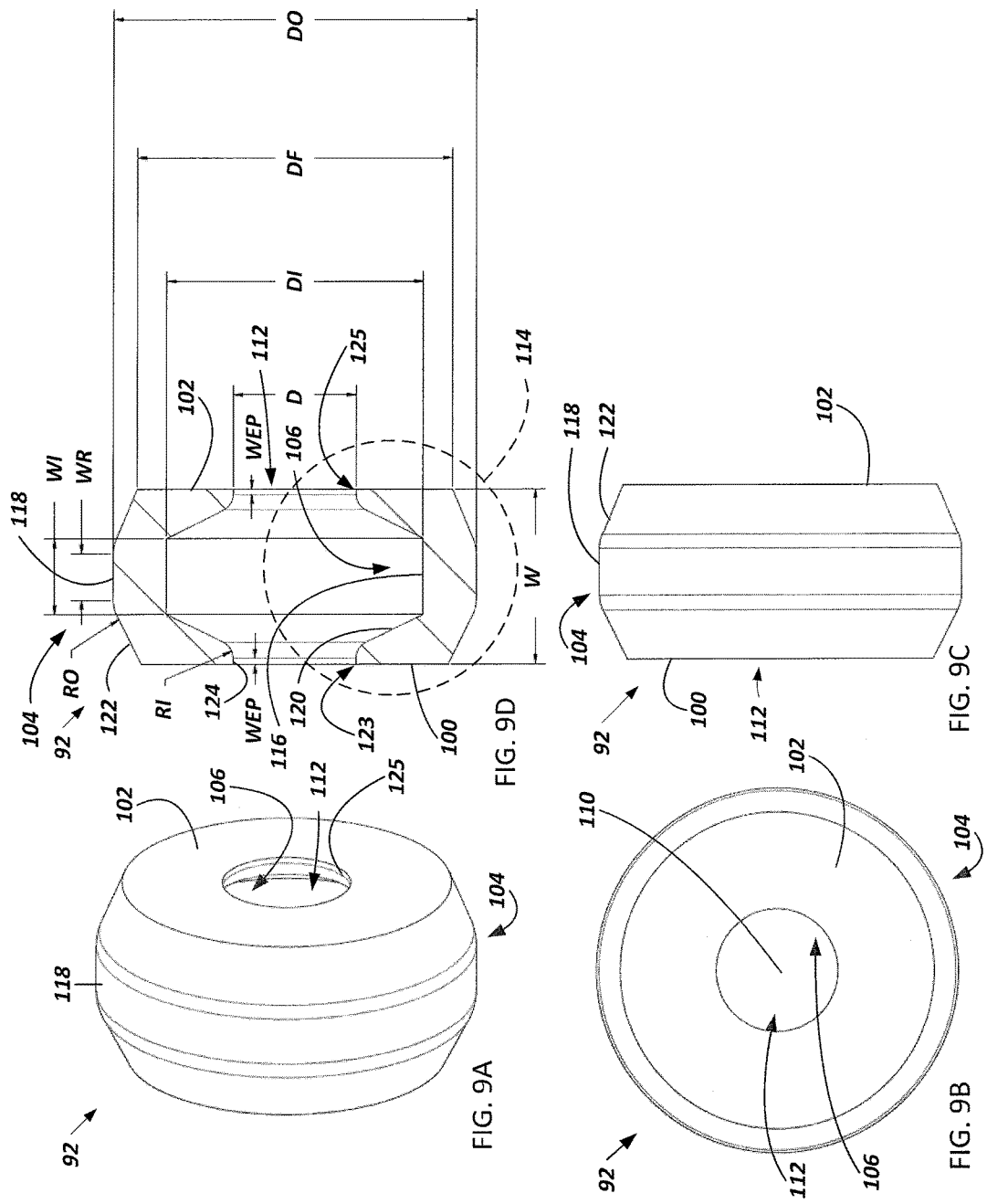

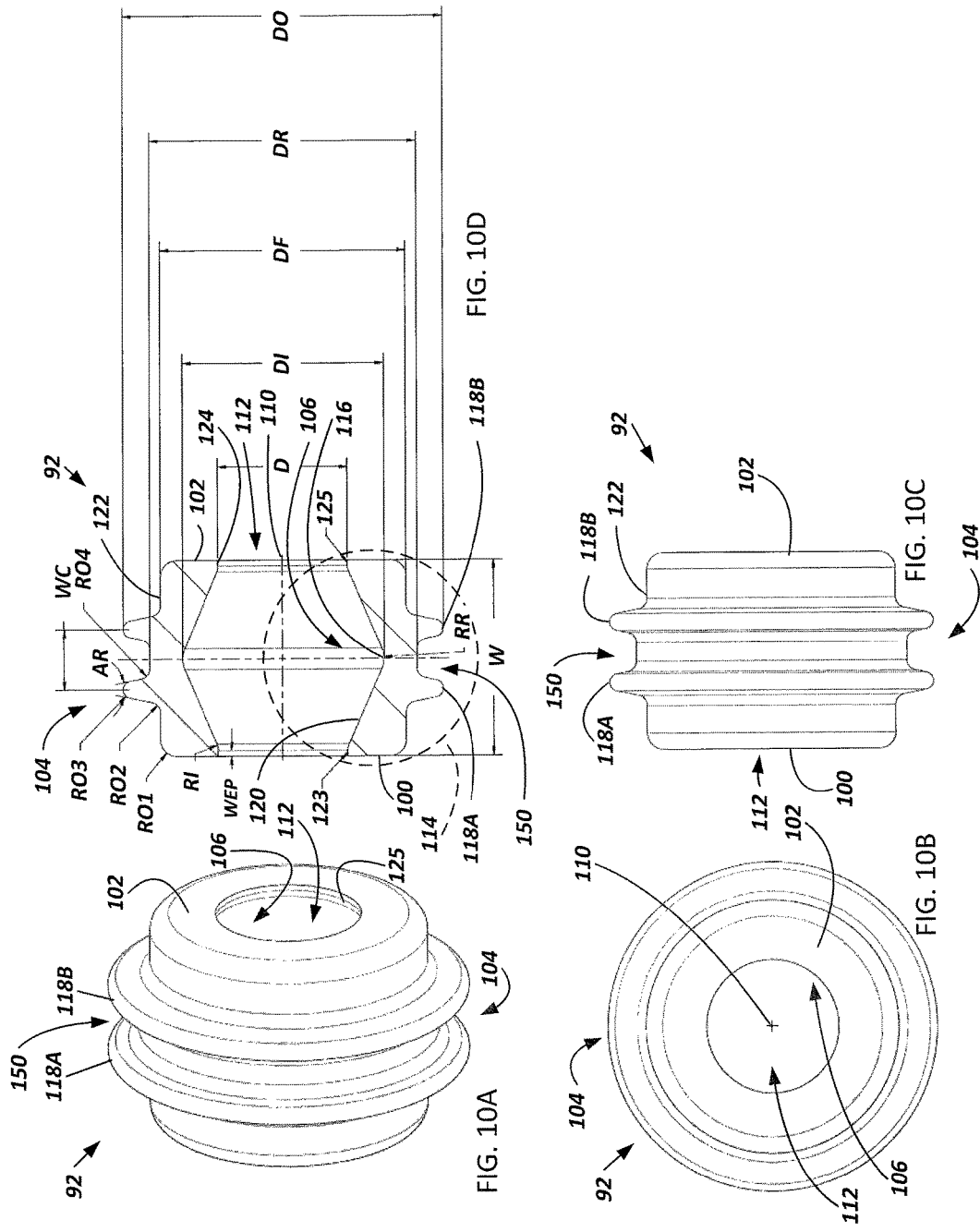

IMPLANTABLE THERAPY LEAD INCLUDING BI-DIRECTIONAL ROTARY BLOOD RING SEAL

FIELD OF THE INVENTION

The present invention relates to medical apparatus and methods. More specifically, the present invention relates to implantable therapy leads.

BACKGROUND OF THE INVENTION

Implantable therapy leads may be configured for active fixation. A common arrangement for a lead configured for active fixation provides a lead distal end with an active fixation helix that extends from the distal end of the lead when a contact pin is rotated at a proximal end of the lead. As the contact pin is rotated about its longitudinal axis, the sharp helix rotates and extends from the lead distal end to screw into myocardial tissue. In some other embodiments, a stylet or other tool is inserted through the lead body to deploy the active fixation helix via rotation and/or sliding distal displacement of the active fixation helix brought about by complementary interaction of the stylet or other tool with structural features of, or associated with, the active fixation helix.

Active fixation implantable therapy leads typically have an inner lumen running from the proximal end of the lead to the distal end of the lead. This lumen is open on both ends of the lead and blood from patients can leak into the lead during implant. Although this blood leakage does not impact the ability of the lead to deliver therapy, blood coagulating inside the lumen can cause difficulty with respect to inserting a stylet into the lead and extending or retracting the helix, all of which can make lead implanting or explanting more difficult.

Complicating any solution to blood leaking into the inner lumen includes the need for the solution to not have an excessive impact on the ability of the helix to extend and retract. Accordingly, there is a need in the art for an active fixation lead that addresses these concerns.

SUMMARY

An implantable therapy lead is disclosed herein. In one embodiment, the therapy lead includes a distal header, a helix-shaft assembly, and a ring seal. The distal header includes a cylindrical passage. The helix-shaft assembly includes a shaft and a helical anchor distally extending from the shaft. The shaft extends through the cylindrical passage. The ring seal circumferentially extends about the shaft and inside the cylindrical passage. The ring seal includes a proximal face, a distal face, an outer circumferential surface, an inner circumferential surface, and a side wall. The distal face is opposite the proximal face. The outer circumferential surface extends between the proximal face and distal face. The inner circumferential surface is opposite the outer circumferential surface and extends between the proximal face and distal face. The inner circumferential surface defines a center hole of the ring seal that extends between the proximal face and distal face. A side wall extends in a continuous ring about the center hole and is defined by the proximal face, the distal face, the outer circumferential surface, and the inner circumferential surface. The side wall includes a radial cross section that is at least generally chevron-shaped.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2 is a longitudinal side view of a distal region of the lead of FIG. 1, wherein the active fixation anchor is shown in the extended or deployed state.

FIG. 3 is a longitudinal cross-section of the distal region of the lead of FIG. 2.

FIGS. 4A-4D are, respectively, an isometric view, end view, side view and side cross sectional view of a first embodiment of a blood ring seal as shown employed in the distal region of the lead in FIG. 3.

FIGS. 5A-5C are, respectively, an end view, side view and side cross sectional view of a second embodiment of a blood ring seal as shown employed in the distal region of the lead in FIG. 3.

FIGS. 6A-6D are, respectively, an isometric view, end view, side view and side cross sectional view of a third embodiment of a blood ring seal as shown employed in the distal region of the lead in FIG. 3.

FIGS. 7A-7D are, respectively, an isometric view, end view, side view and side cross sectional view of a fourth embodiment of a blood ring seal as shown employed in the distal region of the lead in FIG. 3.

FIGS. 8A-8D are, respectively, an isometric view, end view, side view and side cross sectional view of a fifth embodiment of a blood ring seal as shown employed in the distal region of the lead in FIG. 3.

FIGS. 9A-9D are, respectively, an isometric view, end view, side view and side cross sectional view of a sixth embodiment of a blood ring seal as shown employed in the distal region of the lead in FIG. 3.

FIGS. 10A-10D are, respectively, an isometric view, end view, side view and side cross sectional view of a seventh embodiment of a blood ring seal as shown employed in the distal region of the lead in FIG. 3.

DETAILED DESCRIPTION

Figure 1:
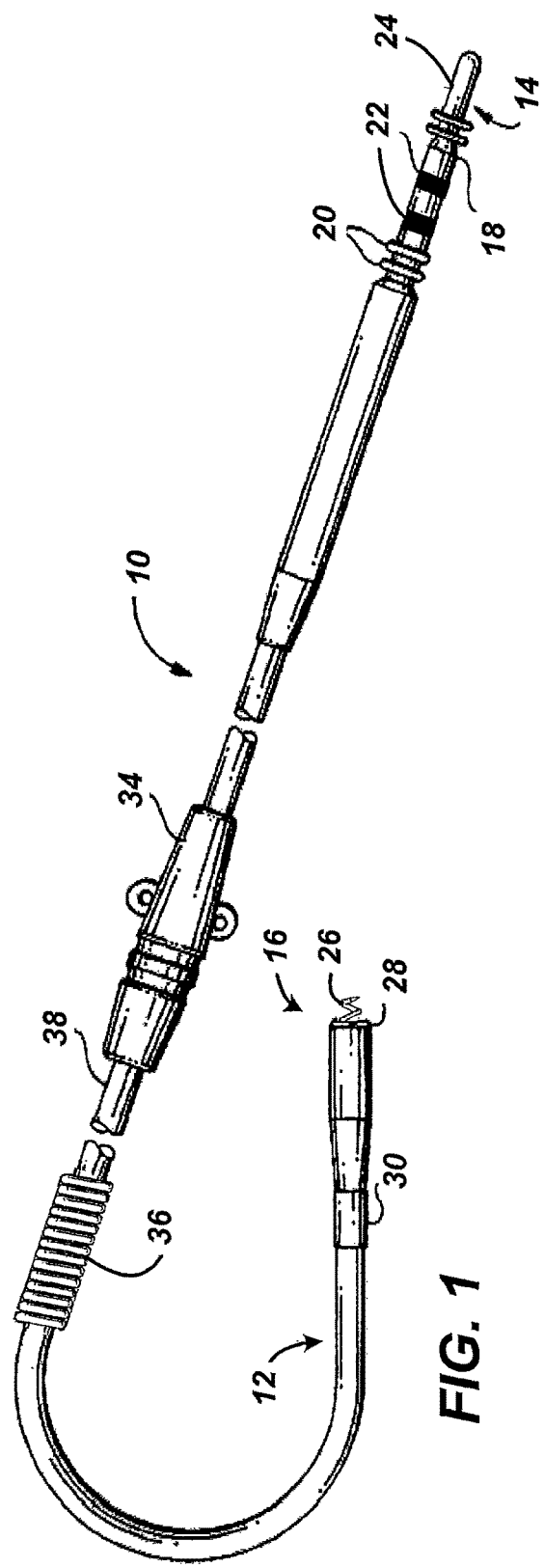
FIG. 1 is a plan view of an embodiment of a lead, wherein an active fixation anchor of the lead is shown in an extended or deployed state.

Implantable therapy leads 10 (e.g., a CRT lead, etc.) and methods of manufacturing such leads are disclosed herein. In one embodiment, the therapy lead 10 is configured for active fixation to heart tissue and includes a blood seal in the form of a ring seal 92 located within the confines of the header 52 and extending about the shaft 58 of the helix-shaft assembly 54.

The shape of ring seal 92 disclosed herein is referred to as a "chevron" or an inverted V-shape in cross section. The seal 92 has a profile that promotes low friction on the helix shaft 58 during helix anchor extension and retraction. This low friction aspect is achieved, at least in part, by the side wall 114 of the seal 92 having a chevron-shaped or inverted V-shaped cross section defining two wide sealing lips 123, 125 that are stretched over the shaft 58 and are allowed to bend without compressing against the header bore. Since there is no direct compression between the header bore and shaft, the ring seal does not exert excessive force on the shaft, thus allowing the shaft to turn with minimal friction.

Unlike typical rotary lip seals, the ring seal 92 disclosed herein can operate with pressure on either side of the seal. The seal is distally-proximally symmetrical and, as a result, can be installed to be oriented in either direction and still operate correctly.

Also, unlike an O-ring, the ring seal 92 disclosed herein does not require a gland or groove in the bore to stay properly oriented. An O-ring without a gland in the bore or shaft will roll on itself during use, causing pre-mature failure of the seal. Even without the use of a gland to keep it in place, the ring seal 92 disclosed herein will stay in place and will resist rolling during use.

1. Overview of Lead

To begin a detailed discussion of the lead 10, reference is made to FIGS. 1 and 2, which are, respectively, a plan view of an embodiment of the lead 10 wherein an active fixation anchor 26 of the lead is shown in an extended or deployed state, and a longitudinal side view of a distal region of the lead of FIG. 1, wherein the active fixation anchor is shown in the extended or deployed state. As can be understood from FIG. 1, the lead 10 is designed for intravenous insertion and contact with the endocardium, and as such, may be conventionally referred to as an endocardial lead. As indicated in FIG. 1, the lead 10 is provided with an elongated lead body 12 that extends between a proximal region 14 and distal region 16 of the lead 10.

The proximal region 14 of the lead 10 includes a connector assembly 18, which is provided with sealing rings 20 and carries at least one or more electrical connectors in the form of ring contacts 22 and a pin contact 24. The connector assembly 18 is configured to be plugged into a receptacle of a pulse generator, the sealing rings 20 forming a fluid-tight seal to prevent the ingress of fluids into the receptacle of the pulse generator. When the connector assembly 18 is plugged into the pulse generator receptacle, the contacts 22, 24 electrically connect with the circuitry of the pulse generator such that electrical signals can be administered and sensed by the pulse generator via the electrical pathways of the lead 10.

The connector assembly 28 is constructed using known techniques and is preferably fabricated of silicone rubber, polyurethane, silicone-rubber-polyurethane-copolymer ("SPC"), or other suitable polymer. The electrical contacts 22, 24 are preferably fabricated of stainless steel or other suitable electrically conductive material that is biocompatible.

As shown in FIGS. 1 and 2, the distal region 16 of the lead 20 includes the helical active fixation anchor 26 distally extending from an extreme distal tip end 28 of the lead 20 when the active fixation anchor 26 is in a deployed state. The anchor 26 may be transitioned to a non-deployed state via retraction of the anchor 26 into the confines of the distal region 16 of the lead 10 or by an obturator or other structural member being combined with the anchor 26 to inhibit the anchor 26 from being able to penetrate tissue.

In one embodiment, the anchor 26 is deployed or placed in the extended state by rotating the contact pin 24, which is coupled via a helical conductor 29 to the anchor 26, as can be understood from FIG. 3, which is a longitudinal cross-section of the distal region of the lead of FIG. 2. As the contact pin 24 is rotated about its longitudinal axis, the helical conductor 29 and sharp helical anchor 26 rotate relative to the rest of the lead 10 to cause the anchor 26 to extend from the lead distal end 28 to screw into myocardial tissue. In some other embodiments, a stylet or other tool is inserted through the lead body 12 to deploy the anchor 26 via rotation and/or sliding distal displacement of the anchor 26 brought about by complementary interaction of the stylet or other tool with structural features of, or associated with, the anchor 26.

The anchor 26 may also be configured to act as an electrode in addition to providing active fixation to heart tissue. Where the anchor 26 is also configured to act as an electrode, depending on the dictates of the pulse generator, the anchor 26 may be employed for sensing electrical energy and/or administration of electrical energy (e.g., pacing). The anchor 26 is electrically coupled to the pin contact 24 of the connector assembly 18 via the electrical conductor 29 extending through the lead body 12 and the connector assembly 18, as can be understood from FIGS. 1 and 3. While the electrical conductor 29 is shown as helically coiled electrical conductors, in other embodiments the conductor 29 may be in the form of wires, cables or other electrical conductors that are linear or helically coiled in configuration.

The distal region 16 of the lead 10 also includes an annular ring electrode 30 proximally offset from the extreme distal tip end 28 of the lead 10. Depending on the dictates of the pulse generator, this ring electrode 30 may be employed for sensing electrical energy and/or administration of electrical energy (e.g., pacing). The ring electrode 30 is electrically coupled to one of the ring contacts 22 of the connector assembly 18 via an electrical conductor 32 extending through the lead body 12 and the connector assembly 18, as can be understood from FIG. 3. While the electrical conductor 32 is shown as helically coiled electrical conductors, in other embodiments the conductor 32 may be in the form of wires, cables or other electrical conductors that are linear or helically coiled in configuration.

As indicated in FIG. 1, the lead 10 may include a fixation sleeve 34 slidably mounted around the lead body 12. The fixation sleeve 34 serves to stabilize the pacing lead 10 at the site of venous insertion.

Where the lead 10 is equipped for defibrillation, a shock coil 36 will be supported on the lead body 12 proximal the ring electrode 30 and distal the fixation sleeve 34. The shock coil 36 is electrically coupled to one of the ring contacts 22 of the connector assembly 18 via electrical conductors extending through the lead body 12 in the form of wires, cables or other electrical conductors that are linear or helically coiled in configuration.

As can be understood from FIGS. 1-3, the lead body 12 includes an outer insulation sheath 38 and an inner insulation sheath 39. The outer insulation sheath 38 is preferably fabricated of silicone rubber, polyurethane, silicone rubber-polyurethane-copolymer (SPC), or other suitable polymer. The inner insulation sheath 39 may be formed of the same material as the outer insulation sheath 39 or from another material such as, for example, polytetrafluoroethylene ("PTFE"). The insulation sheaths 38, 39 isolate the interior components of the lead 10, including the electrical conductors 29, 32, from each other. The outer insulation sheath 38 isolates the inner components of the lead 10 from the surrounding environment and may be single or multi-layer construction.

The lead body 12 is constructed to include a hollow interior or central lumen 40 extending from the proximal region 14 to the distal region 16. The hollow interior allows for the introduction of a stylet, guidewire or other device during implant, which is beneficial in allowing the surgeon to guide the otherwise flexible lead 10 from the point of venous insertion to the myocardium.

As indicated in FIGS. 2 and 3, in one embodiment, the distal region 16 of the lead 10 includes a distal tip assembly 50. The distal tip assembly 50 includes a number of components, such as, for example, a ring electrode 30, a header 52, a helix-shaft assembly 54 and a marker ring assembly 55. The helix-shaft assembly 54 includes a shaft 58 and a helical active fixation anchor 26 extending distally therefrom. The marker ring assembly 55 includes a marker ring 56 and a soft atraumatic tip 57 extending distally therefrom. In one embodiment, the ring electrode 30, header 52, helix-shaft assembly 54 and a marker ring assembly 55 may be secured together via interference fit arrangements, some of which may be in the form of male-female interference fit arrangements including those employing snap-lock arrangements, for example. The helix-shaft assembly 54 is coaxially located within the confines of a cylindrical volume of the header 52.

As can be understood from FIG. 3, the helix-shaft assembly 54 includes its shaft 58 and the helical active fixation anchor 26 extending distally therefrom. The header 52 includes a distal cylindrical passage 60 and proximal cylindrical passage 62 that coaxially intersect with each other at a throat structure 64. The distal passage 60 has a larger diameter than the proximal passage 62.

The throat structure 64 includes a cantilevered ring-like structure 65 that distally projects into the volume of the distal cylindrical passage 60 from the distal boundary of the proximal cylindrical passage 62. The ring-like structure 65 includes a ringed blunt free end 66 that projects distally into the distal passage 60 as part of the cantilevered configuration of the throat structure 64. Opposite the free end 66, the ring-like structure 65 includes a proximally facing surface that extends perpendicularly between the circumferential surface of the proximal passage 62 and a circumferential surface of a throat passage 68 that extends through the throat 64, thereby defining a ringed lip. The throat passage 68 is coaxial with the distal and proximal passages 60, 62, and is smaller in diameter than the proximal passage 62.

As illustrated in FIG. 3, the shaft 58 of the helix-shaft assembly 54 includes a distal shaft portion 70, a distal flange 72, an intermediate shaft portion 74, a throat engagement structure 76, a proximal shaft portion 78, and a proximal flange 80. The diameter of the distal shaft portion 70 is approximately the same size as the intermediate shaft portion 74, which is larger than the diameter of the proximal shaft portion 78. The distal flange 72 separates the distal and intermediate shaft portions. The throat engagement structure 76 and intermediate shaft portion 74 are engaged in a male-female sliding interlocking interference fit arrangement with the throat structure 64.

A proximal portion of the anchor 26 helically extends around the distal shaft portion 70 such that the anchor 26 is coaxial with the distal shaft portion. The proximal end of the anchor 26 abuts against the distal face of the distal flange 72. The anchor 26 distally extends from the distal shaft portion 70. A drug eluding body 73 may be located within the confines of the helical anchor 26 and supported off of the distal shaft portion 70 or distal face of the distal flange 72, the body 73 eluding an anti-inflammatory or other medicament.

The helically wound conductor 29, which extends from and is electrically connected to the pin contact 24 of the connector assembly 18, helically extends about the proximal shaft portion 78. The conductor 29 abuts against the proximal face of the proximal flange 80, which is employed as a weld flange for welding the conductor 29 to the shaft 58. The conductor 29 proximally extends from the proximal shaft portion 78.

The shaft 58 may be formed of an electrically conductive material and serve as an electrical pathway leading between the helical conductor 29 and the helical anchor 26 such that the anchor 26 can serve as an electrode. Methods of establishing an electrical connection between the conductor 29 and the shaft 58 and the anchor 26 and the shaft 58 include, but are not limited to, welding, crimping, etc. While the embodiment depicted herein is discussed in the context of the anchor 26 also serving in an electrode capacity, in other embodiments, the anchor 26 will not have any electrode capacity and will simply serve as an anchoring mechanism.

As can be understood from FIG. 3, the intermediate shaft portion 74 can slide distal-proximal and rotate within the confines of the throat passage 68 of the throat structure 64 in the course of extending/retracting the anchor 26 in the course of effectuating implant/explant. As can be understood from FIG. 3, the distal displacement of the intermediate shaft portion 74 within the throat structure 64 is limited by the abutting of a distal face of the throat engagement structure 76 with a proximal face of the throat structure 64. Oppositely, the proximal displacement of the intermediate shaft portion 74 within the throat structure 64 is limited by the abutting of a proximal face of the distal flange 72 with a distal face of a ring seal 92 that has a proximal face abutting against the ringed blunt free end 66 of the throat structure 64.

As shown in FIG. 3, the ring seal 92 extends about the outer circumferential surface 94 of the intermediate shaft portion 74 in abutting sealing contact and against the inner circumferential surface 96 of the distal passage 60 of the header 52 in abutting sealing contact. A proximal face of the ring seal 92 abuts against the ringed blunt free end 66 of the throat structure 64. The ring seal 92 forms a fluid tight seal against the outer circumferential surface 94 of the intermediate shaft portion 74, the inner circumferential surface 96 of the distal passage 60 of the header 52, and the ringed blunt free end 66 of the throat structure 64.

In some embodiments, the ring seal 92 stays in place against the ringed blunt free end 66 of the throat structure 64 as the intermediate shaft portion 74 displaces distally and proximally through the ring seal 92 and/or rotates within the ring seal. Thus, the displacement of the intermediate shaft portion 74 within the ring seal 92 can be distal/proximal sliding displacement and/or rotational displacement about the longitudinal center axis of the intermediate shaft portion 74, while the outer circumferential surface of the ring seal 92 remains fixed in sealing contact with the 96 inner circumferential surface of the distal passage 60, the inner circumferential surface of the ring seal 92 maintaining displacing, abutting sealing contact with the outer circumferential surface 94 of the intermediate shaft portion 74 despite the displacement of the intermediate shaft portion 74 relative to the ring seal 92.

In some other embodiments, the ring seal 92 stays in place against the intermediate shaft portion 74 as the intermediate shaft portion 74 displaces distally and proximally through the distal passage 60 and throat structure 64 and/or rotates within the distal passage 60 and throat structure 64. Thus, the displacement of the combined intermediate shaft portion 74 and ring seal 92 can be distal/proximal sliding displacement and/or rotational displacement about the longitudinal center axes of the distal passage 60 and throat structure 64, while the inner circumferential surface of the ring seal 92 remains fixed in sealing contact with the outer circumferential surface 94 of the intermediate shaft portion 74, the outer circumference of the ring seal 92 maintaining displacing, abutting sealing contact with the inner circumferential surface 96 of the distal passage 60 despite the displacement of the ring seal 92 relative to the inner circumferential surface of the distal passage 60.

Absent the ring seal 92, a fluid tight seal is not created between the outer circumferential surface 94 of the intermediate shaft portion 74 and the inner circumferential surface of the throat passage 68 of the header 52, nor is a fluid tight seal created between any of the outer circumferential surfaces of the helix-shaft assembly 54 and the inner circumferential surface 96 of the distal passage 60 of the header 52. Thus, absent the ring seal 92, blood would be able to enter the distal passage 60 of the header 52 via the distal end of the lead and pass through the throat passage 68 and into the proximal passage 62 of the header 52, potentially interfering with distal or proximal displacement of the helix 26 during implant or explant of the lead. Since the ring seal 92 creates a fluid tight seal between the intermediate shaft portion 74 and the header 52, no blood can pass proximal the ring seal 92 in the header 52. Since the ring seal 92 maintains its sealing capabilities as the intermediate shaft portion 74 rotates and displaces distal/proximal within the confines of the ring seal 92 in the course of extending or retracting the helix 26, the ring seal 92 can be considered a bi-directional rotary blood ring seal. Further, and as discussed in detail below, the advantageous designs of the different embodiments of the ring seal 92 provide substantial fluid tight sealing capabilities with minimal, if any, adverse impact on the effort required to displace distal/proximal and rotate the helix-shaft assembly 54.

2. Bi-Directional Rotary Blood Ring Seal

FIGS. 4A-4D are, respectively, an isometric view, end view, side view and side cross sectional view of a first embodiment of a bi-directional rotary blood ring seal 92 as shown employed in the distal region 16 of the lead 10. As can be understood from FIGS. 4A-4D, the ring seal 92 includes a proximal face 100, a distal face 102, an outer circumferential surface 104, an inner circumferential surface 106, and a side wall 108. The distal face 102 is opposite the proximal face 100. In one embodiment, one or both of these faces are at least substantially, if not completely, planar. Also, one or both of these faces are at least substantially, if not completely, perpendicular to a center axis 110 of the ring seal 92.

The outer circumferential surface 104 extends between the proximal face 100 and distal face 102. The inner circumferential surface 106 is opposite the outer circumferential surface 104 and extends between the proximal face 100 and distal face 102. The inner circumferential surface defines a center hole 112 of the ring seal 92 that extends between the proximal face and distal face.

As can be understood from FIG. 4D, a side wall 114 extends in a continuous ring about the center hole 112 and is defined by the proximal face 100, the distal face 102, the outer circumferential surface 104, and the inner circumferential surface 106. The side wall 114 includes a radial cross section that is at least generally chevron-shaped.

As shown in FIGS. 4C and 4D, the inner circumferential surface 106 includes a circumferentially extending radially outwardly projecting recess 116, and the outer circumferential surface 104 includes a circumferentially extending radially outwardly projecting ridge 118. The recess 116 includes opposite inner segments 120 that funnel or lead to a most radially outwardly projecting part of the recess 116, and the ridge 118 includes opposite outer segments 122 peaking or leading to a most radially outwardly projecting part of the ridge 118. The pairs of segments 120, 122 are substantially, if not completely, parallel to each other.

The recess 116 defines a recessed region of the chevron-shaped side wall 114. Oppositely, the radially outwardly projecting ridge 118 defines an extreme radially outward point region of the chevron-shaped radial cross section 114.

As indicated in FIG. 4D, in one embodiment, the inner segments 120 and outer segments 122 each form an angle A with the center axis 110 that is approximately 62.9 degrees, plus or minus 10 degrees. The thickness T of the side wall 114 between the inner and outer segments 120, 122 is approximately 0.012", plus or minus 0.004". The radial height H of the side wall 114 at the proximal and distal faces 100, 102 is approximately 0.0195", plus or minus 0.004". The diameter D of the center hole 112 at the proximal and distal faces 100, 102 is approximately 0.023", plus or minus 0.004". The extreme outer diameter DO of the ring seal 92 at the ridge 118 is approximately 0.062", plus or minus 0.002". The width W of the ring seal 92 between the proximal and distal faces 100, 102 is approximately 0.02", plus or minus 0.005".

As can be understood from FIG. 4D, the proximal face 100 and distal face 112 form respective intersections 123, 125 with the surface elements 120, 122 of the inner circumferential surface 106 leading to the circumferentially extending radially outwardly projecting recess 116. These intersections 123, 125 respectively forming a proximal inner circumferential lip 123 and a distal inner circumferential lip 125 distally-proximally separated from each other by the void of the recess 116.

As can be understood from FIGS. 3 and 4D, each lip 123, 125 makes fluid sealing contact with the shaft 58, or more specifically, the outer circumferential surface 94 of the intermediate shaft portion 74 of the shaft 58. Depending on the embodiment, the outer circumferential surface 94 of the intermediate shaft portion 74 is linearly displaceable relative to the lips 123, 125, rotationally displaceable relative to the lips 123, 125, or both. The outer circumferential surface 104 makes fluid sealing contact with the inner circumferential surface 96 of the cylindrical passage 60 of the distal header 52, but does not displace against the inner circumferential surface 96 of the cylindrical passage 60 of the distal header 52 when the shaft 58 displaces relative to the lips 123, 125.

As indicated in FIG. 4D, the recess 116 extends distal-proximal between the lips 123, 125. While each lip 123, 125 makes fluid sealing contact with the shaft 58, the inner circumferential surface 106 corresponding to the recess 116 is spaced radially outward from the shaft 58.

In one embodiment, the ring seal 92 is formed of a medical grade liquid silicone rubber ("LSR") elastomer having a durometer of 55-65. In other embodiments, the ring seal 92 may be made of medical grade LSR having a durometer of 45-83 or medical grade ETR elastomer having a durometer of 45-83.

FIGS. 5A-5C are, respectively, an end view, side view and side cross sectional view of a second embodiment of a bi-directional rotary blood ring seal as shown employed in the distal region 16 of the lead 10. As can be understood from a comparison of the embodiment of FIGS. 4A-4D to the embodiment of FIGS. 5A-5C, these embodiments share many of the same characteristics, including the chevron-shaped cross section of the side wall 114 of the ring seal 92 and the proximal and distal lips 123, 125.

However, there are differences. For example, the embodiment of FIGS. 5A-5C has a more arcuate, deep and narrow circumferentially extending radially outwardly projecting recess 116 defined in the inner circumferential surface 106 of the ring seal 92 than as compared to that of the embodiment of FIGS. 4A-4D. As indicated in FIG. 5C, the inner segments 120 are arcuate and vary in direction and degree of curvature as they extend inwardly from the respective proximal and distal faces 100, 102 to funnel or lead to the most radially outwardly projecting part of the recess 116, which is semi-circular and has a radius R of approximately 0.003", plus 0.003 or minus 0.002". In transitioning from the proximal and distal faces 100, 102, each inner segment 120 begins at an inward edge of a narrow ringed entry portion 124 of the hole 112 that intersects each proximal and distal face 100, 102 and has a surface that is substantially, if not completely, parallel to the center axis 110. The proximal-distal width WEP of each ringed entry portion 124 is approximately 0.001", plus 0.003 or minus 0.001". The entry portions 124 form aspects of the proximal and distal lips 123, 125.

The embodiment of FIGS. 5A-5C has a flatter and wider circumferentially extending radially outwardly projecting ridge 118, which in conjunction with outer segments 122 that are made of a series of short elements that may be angled and flat and/or arcuate, form a more arcuate or rounded outer circumferential surface 104 of the ring seal 92 than as compared to the that of the embodiment of FIGS. 4A-4D. The width WR of the flattened ridge 118 of the rounded outer circumferential surface 104 of the ring seal 92 is approximately 0.005", plus or minus 0.005".

As illustrated in FIG. 5C, the diameter D of the center hole 112 at the proximal and distal faces 100, 102 is approximately 0.023", plus or minus 0.001". The extreme outer diameter DO of the ring seal 92 at the ridge 118 is approximately 0.062", plus or minus 0.003". The extreme inner diameter DI of the recess 116 of the inner circumferential surface 106 is approximately 0.043", plus or minus 0.001". The width W of the ring seal 92 between the proximal and distal faces 100, 102 is approximately 0.02", plus or minus 0.004".

FIGS. 6A-6D are, respectively, an isometric view, end view, side view and side cross sectional view of a third embodiment of a ring seal 92. As can be understood from a comparison of the embodiments of FIGS. 4A-4D and FIGS. 5A-5C to the embodiment of FIGS. 6A-6D, these embodiments share many of the same characteristics, including the chevron-shaped cross section of the side wall 114 of the ring seal 92 and the proximal and distal lips 123, 125. For example, the embodiment of FIGS. 6A-6D employs a combination of aspects of both the embodiments of FIGS. 4A-4D and FIGS. 5A-5C in that the outer circumferential surface 104 has the straight outer segment 122, but arcuately transitions via an outer radius RO to the flatter and wider circumferentially extending radially outwardly projecting ridge 118. Also, the inner circumferential surface 106 includes the straight inner segment 120 leading to, or resulting in, the wider, less deep recess 116. However, the inner and outer segments 120, 122 are not parallel to each other. Also, the inner segments 120 are arcuate and vary in direction and degree of curvature as they extend inwardly from the respective proximal and distal faces 100, 102 to funnel or lead to the most radially outwardly projecting part of the recess 116, which is semi-circular and has a recess radius R.

As can be understood from FIG. 6D, in transitioning from the proximal and distal faces 100, 102, each inner segment 120 begins at an inward edge of a narrow ringed entry portion 124 of the hole 112 that intersects each proximal and distal face 100, 102 and has a surface that is substantially, if not completely, parallel to the center axis 110. The proximal-distal width WEP of each ringed entry portion 124 is approximately 0.001", plus 0.003" or minus 0.001". The entry portions 124 form aspects of the proximal and distal lips 123, 125.

Each narrow ringed entry portion 124 transitions to its immediately adjacent inner segment 120 via an inner radius RI. The recess radius R is approximately 0.005", plus or minus 0.005". The outer radius RO is approximately 0.006", plus or minus 0.005". The inner radius RI is approximately 0.003", plus or minus 0.003". The width WR of the flattened ridge 118 of the outer circumferential surface 104 of the ring seal 92 is approximately 0.008", plus or minus 0.005".

As illustrated in FIG. 6D, the diameter D of the center hole 112 at the proximal and distal faces 100, 102 is approximately 0.024", plus or minus 0.001". The extreme outer diameter DO of the ring seal 92 at the ridge 118 is approximately 0.062", plus or minus 0.003". The extreme inner diameter DI of the recess 116 of the inner circumferential surface 106 is approximately 0.046", plus or minus 0.001". The extreme diameters DF of each proximal and distal face 100, 102 is 0.036", plus or minus 0.003". The width W of the ring seal 92 between the proximal and distal faces 100, 102 is approximately 0.03", plus or minus 0.001".

FIGS. 7A-7D are, respectively, an isometric view, end view, side view and side cross sectional view of a fourth embodiment of a ring seal 92. As can be understood from a comparison of the embodiment of FIGS. 6A-6D to the embodiment of FIGS. 7A-7D, these embodiments are substantially similar, including their chevron-shaped cross sections of the side wall 114 of the ring seal 92 and the proximal and distal lips 123, 125. Some differences between these two embodiments are that the embodiment of FIGS. 7A-7D has two straight outer segments 122 and two outer radii RO1, RO2, which all combine to form the outer circumferential surface 104 of the ring seal 92. A first of the outer segments 122 is straight and forms an angle A1 with its respective face 100, 102 that is approximately 30 degrees, plus or minus 3 degrees. A second of the outer segments 122 is straight and forms an angle A2 with the flattened ridge 118 that is approximately 30 degrees, plus or minus 3 degrees.

As can be understood from FIG. 7D, the proximal-distal width WEP of each ringed entry portion 124 is approximately 0.001", plus or minus 0.0005". The entry portions 124 form aspects of the proximal and distal lips 123, 125.

The recess radius R is approximately 0.008", plus zero inch or minus 0.008". The first outer radius RO1 is approximately 0.006", plus zero inch or minus 0.006". The second outer radius RO2 is approximately 0.005", plus zero inch or minus 0.005". The inner radius RI is approximately 0.003", plus or minus 0.003". The width WR of the flattened ridge 118 of the outer circumferential surface 104 of the ring seal 92 is approximately 0.006", plus or minus 0.001".

As illustrated in FIG. 7D, the diameter D of the center hole 112 at the proximal and distal faces 100, 102 is approximately 0.02", plus or minus 0.001". The extreme inner diameter DI of the recess 116 of the inner circumferential surface 106 is approximately 0.046", plus or minus 0.001". The extreme diameters DF of each proximal and distal face 100, 102 is 0.029", plus or minus 0.001". The width W of the ring seal 92 between the proximal and distal faces 100, 102 is approximately 0.038", plus or minus 0.001".

FIGS. 8A-8D are, respectively, an isometric view, end view, side view and side cross sectional view of a fifth embodiment of a ring seal 92. As can be understood from a comparison of the embodiment of FIGS. 7A-7D to the embodiment of FIGS. 8A-8D, these embodiments share many of the same characteristics, including their chevron-shaped cross sections of the side wall 114 of the ring seal 92 and the proximal and distal lips 123, 125. Some differences between these two embodiments are that the embodiment of FIGS. 8A-8D has a substantially arcuate or curved configuration both interior and exterior such that the inner segment 120 smoothly arcuately transitions from the ringed entry portions 124 to the recess 116 of the inner circumferential surface 106, and the outer segment 122 is also smoothly arcuate extending from the respective faces 100, 102 to the flattened ridge 118 of the outer circumferential surface 104.

As can be understood from FIG. 80D, the inner circumferential surface 106 transitions from the ringed entry portions 124 to an inner transition radius RI that then transitions to the recess radius R, which extends in a constant manner along the entirety of the recess 116 between the inner transition radii RI. The outer segments 122 are arcuate along their extent between their respective faces 100, 102 to the flattened ridge 118, each segment 122 having a constant outer radius RO.

As can be understood from FIG. 8D, the proximal-distal width WEP of each ringed entry portion 124 is approximately 0.001", plus or minus 0.0005". The entry portions 124 form aspects of the proximal and distal lips 123, 125.

The recess radius R is approximately 0.017", plus or minus 0.005". The outer radius RO is approximately 0.016", plus or minus 0.005". The inner radius RI is approximately 0.002", plus or minus 0.002". The width WR of the flattened ridge 118 of the outer circumferential surface 104 of the ring seal 92 is approximately 0.006", plus or minus 0.001".

As illustrated in FIG. 8D, the extreme diameters DF of each proximal and distal face 100, 102 is 0.03", plus or minus 0.001". The extreme outer diameter DO of the ring seal 92 at the ridge 118 is approximately 0.062", plus or minus 0.003". The width W of the ring seal 92 between the proximal and distal faces 100, 102 is approximately 0.038", plus or minus 0.001".

FIGS. 9A-9D are, respectively, an isometric view, end view, side view and side cross sectional view of a sixth embodiment of a ring seal 92. As can be understood from a comparison of the embodiment of FIGS. 6A-6D to the embodiment of FIGS. 9A-9D, these embodiments share many of the same characteristics, including their chevron-shaped cross sections of the side wall 114 of the ring seal 92 and the proximal and distal lips 123, 125. Some differences between these two embodiments are that the embodiment of FIGS. 9A-9D has a substantially angular configuration both interior and exterior such that the inner segment 120 is straight and makes an angled transition to the extreme extent of the recess 116 of the inner circumferential surface 106, and the outer segment 122 is also straight extending from the respective faces 100, 102 to a narrow accurate transition having an outer radius RO just before intersecting the flattened ridge 118 of the outer circumferential surface 104.

As can be understood from FIG. 9D, the proximal-distal width WEP of each ringed entry portion 124 is approximately 0.001", plus 0.005 or minus 0.001". The entry portions 124 form aspects of the proximal and distal lips 123, 125.

The inner width WI of the recess 116 is approximately 0.013", plus or minus 0.003". The outer radius RO is approximately 0.006", plus or minus 0.005". The inner radius RI is approximately 0.003", plus or minus 0.003". The width WR of the flattened ridge 118 of the outer circumferential surface 104 of the ring seal 92 is approximately 0.008", plus or minus 0.001".

As illustrated in FIG. 9D, the diameter D of the center hole 112 at the proximal and distal faces 100, 102 is approximately 0.020", plus or minus 0.001". The extreme diameters DF of each proximal and distal face 100, 102 is 0.054", plus 0.001" or minus 0.002". The extreme outer diameter DO of the ring seal 92 at the ridge 118 is approximately 0.062", plus or minus 0.003". The extreme inner diameter DI of the recess 116 of the inner circumferential surface 106 is approximately 0.044", plus 0.001 or minus 0.005". The width W of the ring seal 92 between the proximal and distal faces 100, 102 is approximately 0.03", plus 0.001" or minus 0.002".

FIGS. 10A-10D are, respectively, an isometric view, end view, side view and side cross sectional view of a seventh embodiment of a ring seal 92. The embodiment of FIGS. 10A-10D shares many of the same characteristics of the previously discussed embodiments, including their chevron-shaped cross sections of the side wall 114 of the ring seal 92 and the proximal and distal lips 123, 125. However, unlike the previously discussed embodiments, the outer circumferential surface 104 of the embodiment of FIGS. 10A-10D includes first and second circumferentially extending radially outwardly projecting ridges 118A, 118B that are offset from each other by a centered width WC of approximately 0.0114", plus or minus 0.001". The offset ridges 118A, 118B define in the outer circumferential surface 104 a radially inward extending recess 150 between the first and second ridges 118A, 118B.

As best understood from FIGS. 10C and 10D, the proximal and distal faces 100, 102 transition to the outer segment 122 of the outer circumferential surface 104 via a first radius RO1 of approximately 0.003", plus or minus 0.003". The outer segment 122 is substantially, if not completely, parallel to the center axis 110 of the ring seal 92. The outer segments 122 transition to sloped faces of the respective ridges 118A, 118B via a second radius RO2 of approximately 0.002", plus or minus 0.002". The proximal and distal pairs of sloped faces forming the sides of each ridge 118A, 118B form an angle AR with each other of approximately 23.5 degrees, plus or minus 5 degrees. The radial outer edge of each ridge 118A, 118B has a radius RO3 of approximately 0.003", plus or minus 0.001". Each opposing sloped face of the ridges 118A, 118B defining the recess 150 transitions to a bottom or most radially inward surface of the recess 150 via a radius RO4 of approximately 0.002", plus or minus 0.002".

As can be understood from FIG. 10D, the proximal-distal width WEP of each ringed entry portion 124 is approximately 0.001", plus or minus 0.0005". The entry portions 124 form aspects of the proximal and distal lips 123, 125. The radius transition RI from the entry portions 124 to the inner segment 120 is approximately 0.003", plus or minus 0.003". The extreme bottom or apex of the recess 116 has a radius RR between the inner segments 120 of approximately 0.005", plus or minus 0.005".

As illustrated in FIG. 10D, the diameter D of the center hole 112 at the proximal and distal faces 100, 102 is approximately 0.024", plus or minus 0.001". The extreme diameters DF of each proximal and distal face 100, 102 is 0.046", plus or minus 0.001". The extreme outer diameter DO of the ring seal 92 at the ridges 118A, 118B is approximately 0.06", plus or minus 0.001". The outer diameter DR of the ring seal 92 at the bottom of the recess 150 is approximately 0.05", plus or minus 0.001". The extreme inner diameter DI of the recess 116 of the inner circumferential surface 106 is approximately 0.038", plus or minus 0.001". The width W of the ring seal 92 between the proximal and distal faces 100, 102 is approximately 0.037", plus or minus 0.001".

As can be understood from a review of all the embodiments of FIGS. 4A-10D, the inner segments 120 of the inner circumferential surface 106 of the ring seal 92 slope outwardly towards the respective proximal and distal faces 100, 102 such that the lips 123, 125 can be said to be spaced wide apart plus angled both radially inward and proximally-distally outward. In other words, the proximal lip 123 is angled both radially inward and proximally outward. Similarly, the distal lip 125 is angled both radially inward and distally outward. As a result of the angled and widely spaced lips 123, 125, the seal 92 is less likely to be simultaneously compressed against the shaft and inner circumferential surface of the header, thereby providing for low friction between the seal and the header surface.

As can be understood from FIGS. 4D, 5C, 6D, 7D, 8D, 9D and 10D, the ringed seal 92 is also symmetrical proximal-distal. As a result, the seal 92 is bi-directional and can be installed in the header 52 in either direction and still function properly.

While the ring seal 92 is depicted as being employed in the lead distal end of FIG. 3, the ring seal 92 can be implemented in any lead that has a helix shaft and header bore. During assembly, the ring seal 92 is installed on the helix shaft and pushed into the header bore during assembly. Once placed in the header bore the seal will maintain its position relative to the header bore as the shaft moves back and forth distal-proximal, as can be understood from FIG. 3.

Since the sealing lips are stretched over the shaft and the seal is pressed into the header bore, the seal prevents body fluid (e.g., blood) from entering the inner lumen. Since the compression against the header bore does not translate to the helix shaft, the shaft rotates with minimal friction.

The seal embodiments disclosed herein are capable of sealing up to 30 mmHg pressure in water, which is a pressure typical for the right ventricle pressure during systole and is the maximum pressure such leads are likely to experience. The seal embodiments disclosed herein are able to seal up to 30 psi in air. Air and water have lower viscosities than blood, meaning they are more likely to leak given the same initial conditions.

The seals disclosed prevent blood from entering the inner lumen of the lead and, as a result, the seals disclosed herein will prevent the helical anchor from performing poorly sue to the inner lumen being filled with coagulated blood. The seals disclosed herein will also maintain low friction against the helix shaft to have minimal impact to helix extension/retraction performance.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. An implantable therapy lead comprising:
   a distal header having a cylindrical passage;
   a helix-shaft assembly having a shaft and a helical anchor distally extending from the shaft, the shaft extending through the cylindrical passage; and
   a ring seal circumferentially extending about the shaft and inside the cylindrical passage, the ring seal comprising:
   a proximal face defining a proximal opening;
   a distal face opposite the proximal face and defining a distal opening;
   an outer circumferential surface extending between the proximal face and distal face;
   an inner circumferential surface opposite the outer circumferential surface and extending between the proximal face and distal face, the inner circumferential surface defining a center hole of the ring seal that extends between the proximal opening and the distal opening; and
   a side wall extending in a continuous ring about the center hole and defined by the proximal face, the distal face, the outer circumferential surface, and the inner circumferential surface, the side wall having a radial cross section that is at least generally chevron-shaped,
   wherein the inner circumferential surface defines a recess of the chevron-shaped radial cross section, the recess having a radial extent greater than that of each of the proximal opening and the distal opening.

2. The lead of claim 1, wherein the inner circumferential surface further comprises a proximal inner circumferential lip and a distal inner circumferential lip, and the recessed region extends distal-proximal between the lips.

3. The lead of claim 2, wherein each lip makes fluid sealing contact with the shaft, and the inner circumferential surface corresponding to the recess region is spaced radially outward from the shaft.

4. The lead of claim 3, wherein the shaft is at least one of linearly displaceable relative to the lips or rotationally displaceable relative to the lips.

5. The lead of claim 4, wherein the outer circumferential surface does not displace against an inner circumferential surface of the cylindrical passage of the distal header when the shaft displaces relative to the lips.

6. The lead of claim 2, wherein the proximal inner circumferential lip intersects the proximal face, and the distal inner circumferential lip intersects the distal face.

7. The lead of claim 1, wherein the proximal face and distal face form respective intersections with surface elements of the inner circumferential surface leading to the circumferentially extending radially outwardly projecting recess, the intersections respectively forming a proximal inner circumferential lip and a distal inner circumferential lip.

8. The lead of claim 7, wherein each lip makes fluid sealing contact with the shaft.

9. The lead of claim 8, wherein the shaft is at least one of linearly displaceable relative to the lips or rotationally displaceable relative to the lips.

10. The lead of claim 9, wherein the outer circumferential surface does not displace against an inner circumferential surface of the cylindrical passage of the distal header when the shaft displaces relative to the lips.

11. The lead of claim 1, wherein the outer circumferential surface comprises a circumferentially extending radially outwardly projecting ridge that defines an extreme radially outward point region of the chevron-shaped radial cross section.

12. The lead of claim 11, wherein the recess comprises a first segment leading to a most radially outwardly projecting part of the recess, and the ridge comprises a second segment leading to a most radially outwardly projecting part of the ridge, the first and second segments being parallel to each other.

13. The lead of claim 1, wherein the outer circumferential surface comprises first and second circumferentially extending radially outwardly projecting ridges that are offset from each other.

14. The lead of claim 13, wherein the outer circumferential surface further comprises a radially inward extending recess between the first and second ridges.

15. The lead of claim 1, wherein the inner circumferential surface comprises:
- a proximal inner circumferential segment extending partially radially outwardly; and
- a distal inner circumferential segment opposite the proximal inner circumferential segment and extending partially radially outwardly, wherein a most radially outwardly protecting portion of the recess is disposed between the proximal inner circumferential segment and the distal inner circumferential segment.

16. The lead of claim 1, wherein the radial cross section of the side wall defines inner segments of the inner circumferential surface that slope outwardly towards the respective proximal and distal faces to define respective proximal and distal circumferentially extending radially inward projecting sealing lips.

17. The lead of claim 1, wherein the radial cross section of the side wall defines proximal and distal sealing lips that are spaced apart and angled both radially inward and proximally-distally outward.

18. The lead of claim 1, wherein the radial cross section of the side wall defines a proximal sealing lip and a distal sealing lip, the proximal lip being angled both radially inward and proximally outward, and the distal lip being angled both radially inward and distally outward.

19. The lead of claim 1, wherein the ring seal is symmetrical proximal-distal.

20. The lead of claim 1, wherein the ring seal is capable of sealing up to approximately 30 mmHg pressure in water.

* * * * *